US008329396B1

(12) United States Patent
Alizon et al.

(10) Patent No.: US 8,329,396 B1
(45) Date of Patent: Dec. 11, 2012

(54) CLONED DNA SEQUENCES HYBRIDIZABLE WITH GENOMIC RNA OF LYMPHADENOPATHY ASSOCIATED VIRUS (LAV)

(75) Inventors: Marc Alizon, Paris (FR); Francoise Barre Sinoussi, Clamart (FR); Pierre Sonigo, Paris (FR); Pierre Tiollais, Paris (FR); Jean-Claude Chermann, Cassis (FR); Luc Montagnier, Le Plessis Robinson (FR); Simon Wain-Hobson, Montigny le Bretonneux (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 08/052,728

(22) Filed: Apr. 27, 1993

Related U.S. Application Data

(63) Continuation of application No. 07/499,210, filed on Mar. 19, 1990, now abandoned, which is a continuation of application No. 06/771,230, filed on Aug. 30, 1985, now abandoned, which is a continuation-in-part of application No. 06/706,562, filed on Feb. 28, 1985, now abandoned, which is a continuation-in-part of application No. 06/558,109, filed on Dec. 5, 1983, now abandoned.

(30) Foreign Application Priority Data

| Sep. 15, 1983 | (GB) | ..................................... | 8324800 |
| Sep. 6, 1984 | (ZA) | ..................................... | 84/7005 |
| Sep. 19, 1984 | (GB) | ..................................... | 8423659 |

(51) Int. Cl.
*C12Q 1/68* (2006.01)
*C07H 21/02* (2006.01)
(52) U.S. Cl. ..................................... 435/6.1; 536/23.72
(58) Field of Classification Search .................. 536/23.1; 435/5, 6, 320.1, 252.3, 240.2, 236, 91.1
See application file for complete search history.

(56) References Cited

U.S. PATENT DOCUMENTS

| 4,520,113 A | 5/1985 | Gallo et al. | ........................ 435/5 |
| 4,629,783 A | 12/1986 | Cosand | ........................ 530/324 |
| 4,661,445 A | 4/1987 | Saxinger et al. | .................. 435/5 |
| 4,708,818 A | 11/1987 | Montagnier et al. | .............. 435/5 |
| 4,716,102 A | 12/1987 | Levy | ........................ 435/5 |
| 4,725,669 A | 2/1988 | Essex et al. | .................. 530/322 |
| 5,135,864 A | 8/1992 | Montagnier et al. | ....... 435/235.1 |
| 5,156,949 A | 10/1992 | Luciw et al. | ........................ 435/5 |

FOREIGN PATENT DOCUMENTS

| EP | 0 173 529 | 3/1986 |
| EP | 0 199 301 | 10/1986 |
| EP | 0 230 784 | 8/1987 |
| EP | 0 249 390 | 12/1987 |
| EP | 0 249 394 | 12/1987 |
| WO | WO 85/04903 | 11/1985 |
| WO | WO 86/01535 | 3/1986 |

OTHER PUBLICATIONS

*Molecular Cloning: A Laboratory Manual*, T. Maniatis et al, Eds. Cold Spring Harbor Labratory, N.Y., 1982, pp. 24, 211-223.*
Gelmann et al., "Molecular Cloning of a Unique Human T-cell Leukemia Virus (HTLV-II$_{Mo}$)", *Proc. Natl. Acad. Sci.*, USA, 81, 993-997 (1984).
Barre-Sinoussi et al., "Isolation of A T-Lymphotropic Retrovirus From a Patient at Risk for Acquired Immune Deficiency Syndrom (AIDS)", *Science*, 220, 868-871 (1983).
Alizon et al., "Molecular Cloning of Lymphadenopathy-Associated Virus", *Nature*, 312, 757-760 (1984).
Arya et al., "Homology of Genome of AIDS-Associated Virus with Genomes of Human T-Cell Leukemia Viruses", *Science*, 225, 927-930 (1984).
Gelmann et al, "Proviral DNA of a Retrovirus, Human T-Cell Leukemia Virus, in Two Patients with ADS", *Science*, 220, 862-865 (1983).
Hahn et al., "Molecular Cloning and Characterization of the HTLV-III Virus Associated with AIDS", *Nature*, 312, 166-169 (1984).
Shaw et al., "Molecular Characterization of Human T-Cell Leukemia (Lymphotropic) Virus Type III in the Acquired Immune Deficiency Syndrome", *Science*, 226, 1165-1171 (1984).
Kalyanaraman et al., "Antibodies to the Core Protein of Lymphadenopathy Associated Virus (LAV) in Patients With AIDS", *Science*, 225, 321-323, (1984).
Scheupbach et al., "Serological Analysis of a Subgroup of Human T-Lymphotropic Retroviruses (HTLV-III) Associated with AIDS", *Science*, 224, 503-505 (1984).
Sarngadharan et al.. "Antibodies reactive with Human T-Lymphotropic Retroviruses (HTLV-III) in the Serum of Patients with AIDS", *Science*, 224, 506-508 (1984).
Wain-Hobson et al., "Nucleotide Sequence of the AIDS Virus, LAV", *Cell*, 40, 9-17 (1985).
Montagnier et al., "Adaptation of Lymphadenopathy Associated Virus (LAV) to Replication in EBV-Transformed B Lymphoblastoid Cell Lines", *Science*, 225, 63-66 (1984).
Chang et al., "Expression in *Escherichia coli* of Open Reading Frame Gene Segments of HTVL-III", *Science*, 228, 93-96 (1985). Chang et al.. "An HTLV-III peptide produced by recombinant DNA is immunoreactive with sera from patients with AIDS", *Nature*, 315, 151-154 (1985).
Ratner et al., "Complete Nucleotide Sequence of the AIDS Virus, HTLV-III", *Nature*, 313, 277-284 (1985).
Safai et al., "Seroepidemiological Studies of Human T-Lymphotropic Retrovirus Type III in Acquired Immunodeficiency Syndrome", *The Lancet*, 1438-1440 (Jun. 30, 1984).

* cited by examiner

*Primary Examiner* — Christopher M. Babic
(74) *Attorney, Agent, or Firm* — Law Office of Salvatore Arrigo and Scott Lee, LLP

(57) ABSTRACT

This invention is in the field of lymphadenopathy virus. This invention relates to a diagnostic means and method of detecting lymphadenopathy associated virus or related viruses or DNA pro-viruses with cloned DNA sequences which are hybridizable to genomic RNA and DNA of lymphadenopathy associated virus. It further relates to the cloned DNA sequences and a process for their preparation.

27 Claims, 2 Drawing Sheets

Figure 1:
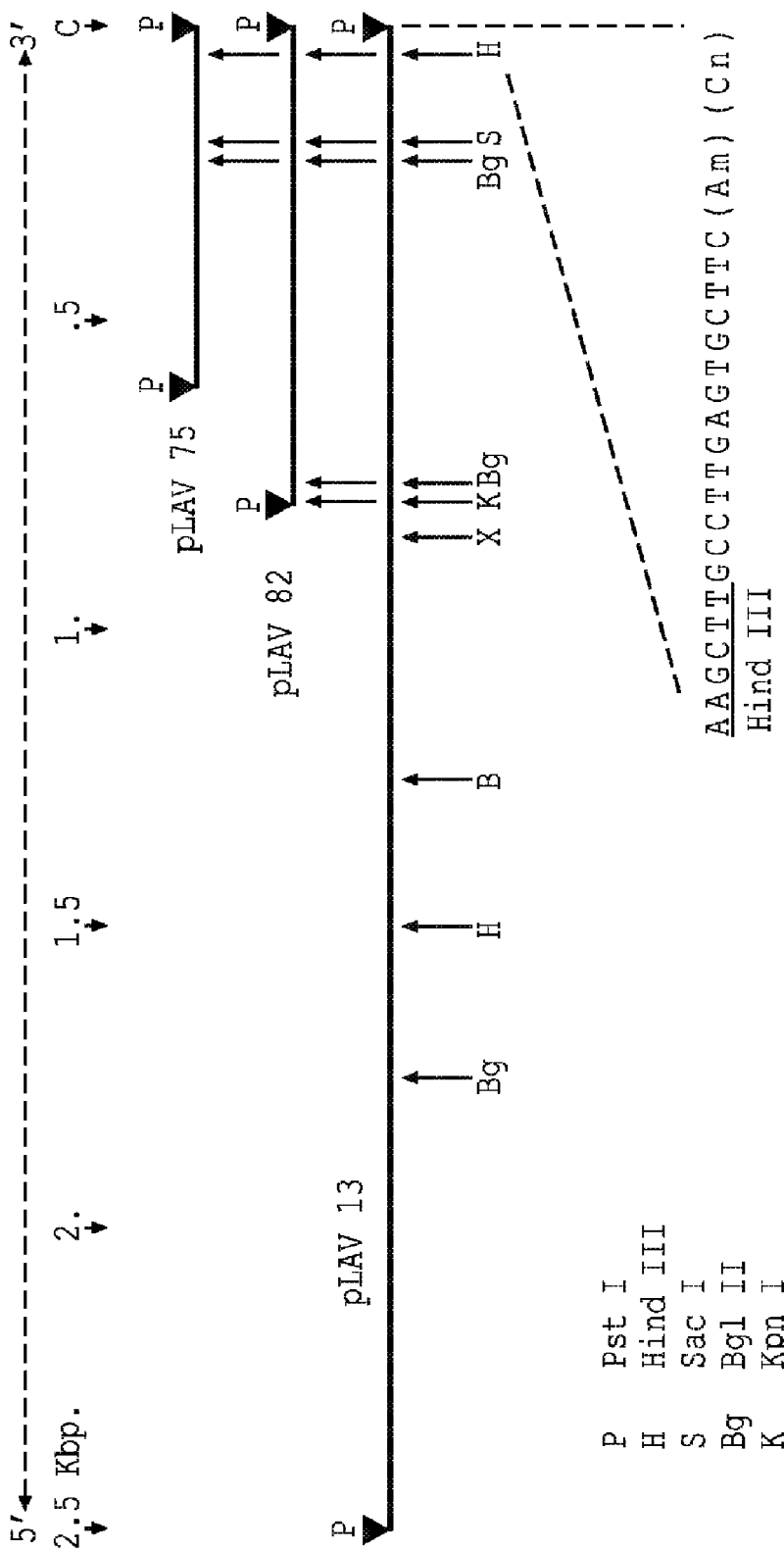

CLONED DNA SEQUENCES HYBRIDIZABLE WITH GENOMIC RNA OF LYMPHADENOPATHY ASSOCIATED VIRUS (LAV)

CROSS-REFERENCE TO RELATED APPLICATIONS

This application is a continuation of application Ser. No. 07/499,210, filed Mar. 19, 1990, which is a continuation of application Ser. No. 06/771,230, filed Aug. 20, 1985, now abandoned, which is a continuation of application Ser. No. 06/706,562, filed Feb. 28, 1985, now abandoned, which is a continuation-in-part of application Ser. No. 06/558,109, filed Dec. 5, 1983, now abandoned.

BACKGROUND OF THE INVENTION

The invention relates to cloned DNA sequences hybridizable to genomic RNA and DNA of lymphadenopathy-associated virus (LAV), a process for their preparation and their uses. It relates more particularly to stable probes including a DNA sequence which can be used for the detection of the LAV virus or related viruses or DNA pro-viruses in any medium, particularly biological, samples containing any of them.

Lymphadenopathy-associated virus (LAV) is a human retrovirus first isolated from the lymph node of a homosexual patient with lymphadenopathy syndrome, frequently a prodrome or a benign form of acquired immune deficiency syndrome (AIDS) (cf. 1). Subsequently, other LAV isolates have been recovered from patients with AIDS or pre-AIDS (cf. 2-5). All available data are consistent with the virus being the causative agent of AIDS (cf. 11).

The virus is propagated on activated T lymphocytes and has a tropism for the T-cell subset OKT4 (cf. 2-5), in which it induces a cytopathic effect. However, it has been adapted for growth in some Epstein-Barr virus transformed B-cell lines (cf. 7), as well as in the established T-lymphoblastic cell line, CEM.

LAV-like viruses have more recently been independently isolated from patients with AIDS and pre-AIDS. These viruses called HTLV-III (Human T-cell Leukemia/Lymphoma virus type III (cf. 12-15) and ARV (AIDS-associated retrovirus) seem to have many characteristics similar to those of LAV and it is thus probable that they represent independent isolates of the LAC prototype.

Detection methods so far available are based on the recognition of core proteins. Such a method is disclosed in European application titled "Antigenes, moyens et methode pour le diagnostic de lymphadenopathie et du syndrome d'immunodepression acquise" field on Sep. 14, 1984, under the priority of British application Serial Nr. 83 24000, filed on Sep. 15, 1983. As a matter of fact, a high prevalence of anti-p25 antibodies has been found in the sera of AIDS and pre-AIDS patients and to a lesser, but significant extent in the high-risk groups for AIDS (cf. 8-10). However, the same sera were found not to recognize the virus as a whole, in a non-disintegrated state.

SUMMARY OF THE INVENTION

The present invention aims at providing new means which should not only also be useful for the detection of LAV or related viruses (hereafter more generally referred to as "LAV viruses"), but also have more versatility, particularly in detecting specific parts of the genomic DNA of said viruses whose expression products are not always detectable by immunological methods.

The DNAs according to the invention consist of DNAs which contain DNA fragments, hybridizable with the genomic RNA of LAV. Particularly said DNAs consist of said cDNAs or cDNA fragments or of recombinant DNAs containing said cDNAs or cDNA fragments. Preferred cloned cDNA fragments respectively contain the following restriction sites in the respective orders which follow (from the 3' end to the 5' end):
1) HindIII, SacI, BglII (LAV75)
2) HindIII, SacI, BglII, BglII, KpnI (LAV82)
3) HindIII, SacI, BglII, BglII, KpnI, XhoI, BamHI, HindIII, BglII (LAV13).

The LAV75, LAV82 and LAC13 designations correspond to the designations of the recombinant plasmids designated as pLAV 75, pLAV 82 and pLAV13, respectively, in which they were first cloned. In other words, LAV 75, LAV 82 and LAV 13, respectively, are present as inserts in said recombinant plasmids. For convenience, the designations LAV 75, LAV 82 and LAV 13 will be further used throughout this specification to designate the cDNA fragments, whether the latter are in isolated for or in plasmid form, whereby the other DNA parts of said last mentioned recombinants are identical to or different from the corresponding parts of pLAV 75, pLAV 82 and pLAV 13, respectively.

Preferred cDNAs also (like LAV 75, LAV 82 and LAV 13) contain a region corresponding to the R and U 3 regions of the LTR (Long Terminal Repeat) as well as the 3' end of the coding region of the retroviral DNA, particularly if it is assumed that the retroviral structure of LAV is in general agreement with the retroviral genomic structures to date.

LAV 13, which has a size of about 2.5 Kbp, has been found of particular advantage. It is highly specific of LAV or LAV related viruses and also recognizes more of the LAV retroviral genomes than do LAV75 or LAV82. Particularly, LAV 13 enabled the identification of the RU 5 junction of the retroviral genomes within the LTR and, subsequently, the sizes of the LAV genomes, which average from about 9.1 to about 9.2 kb.

LAV 13 is free of restriction sites for the following enzymes Eco RI, Nru I, Pvu I, Sal I, Sma I, Sph I, Stu I and Xba I.

LAV 13 further appears to contain at least part of the DNA sequences corresponding to those which, in retroviral genomes, code for the envelope protein.

The invention further relates to any of the fragments contained in the cDNA which seems to correspond to part of the whole of the LAV retroviral genome, which is characterized by a series of restriction sites in the order hereafter (from the 5' end to the 3' end).

The coordinates of the successive sites of the whole LAV genome (restriction map) are indicated hereafter too, with respect to the Hind III site (selected as of coordinate 1), which is located in the R region. The coordinates are estimated to within ±200 bp. Some coordinates are better established then others.

| Hind III | 0 |
| Sac I | 50 |
| Bam HI | 460 |
| Hind III | 520 |
| Bam HI | 600 |
| Pst I | 800 |

| | |
|---|---|
| Hind III | 1 100 |
| Bgl II | 1 500 |
| Kpn I | 3 500 |
| Kpn I | 3 900 |
| Eco RI | 4 100 |
| Eco RI | 5 300 |
| Sal I | 5 500 |
| Kpn I | 6 100 |
| Bgl II | 6 500 |
| Bgl II | 7 600 |
| Hind III | 7 850 |
| Bam HI | 8 150 |
| Xho I | 8 600 |
| Kpn I | 8 700 |
| Bgl II | 8 750 |
| Bgl II | 9 150 |
| Sac I | 9 200 |
| Hind III | 9 250 |

The abovesaid DNA according to the invention optionally contains an additional Hind III approximately at the 5 550 coordinate.

The invention further relates to other preferred DNA fragments corresponding substantially to those which in relation to the abovesaid restriction map extend respectively:

from approximately Kpn I (6 100) to approximately Bgl II (9150) said fragment being thought to correspond at least in part to the gene coding for the proteins of the envelope: in particular a protein p110 of about 110,000 Daltons is needed by this region;

from approximately Kpn I (3 500) to approximately Bgl II (6500), said fragment being thought to correspond at least in part to the pol gene, coding for the virus polymerase;

from approximately Pst I (800) to approximately Kpn I (3500), said fragment being thought to correspond at least in part to the gag gene, which codes for the core antigens, including the p25, the p18, and the p13 proteins.

More particularly, the invention relates to any fragment corresponding to the above ones, having substantially the same sites at substantially same distances from one another, all of these fragments having in common the capability of hybridizing with the LAV retroviral genomes. It is of course understood that fragments which would include some deletions or mutation which would not substantially alter their capability of also hybridizing with the LAV retroviral genomes are to be considered as forming obvious equivalents of the DNA fragments more specifically referred to hereabove.

Figure 2:
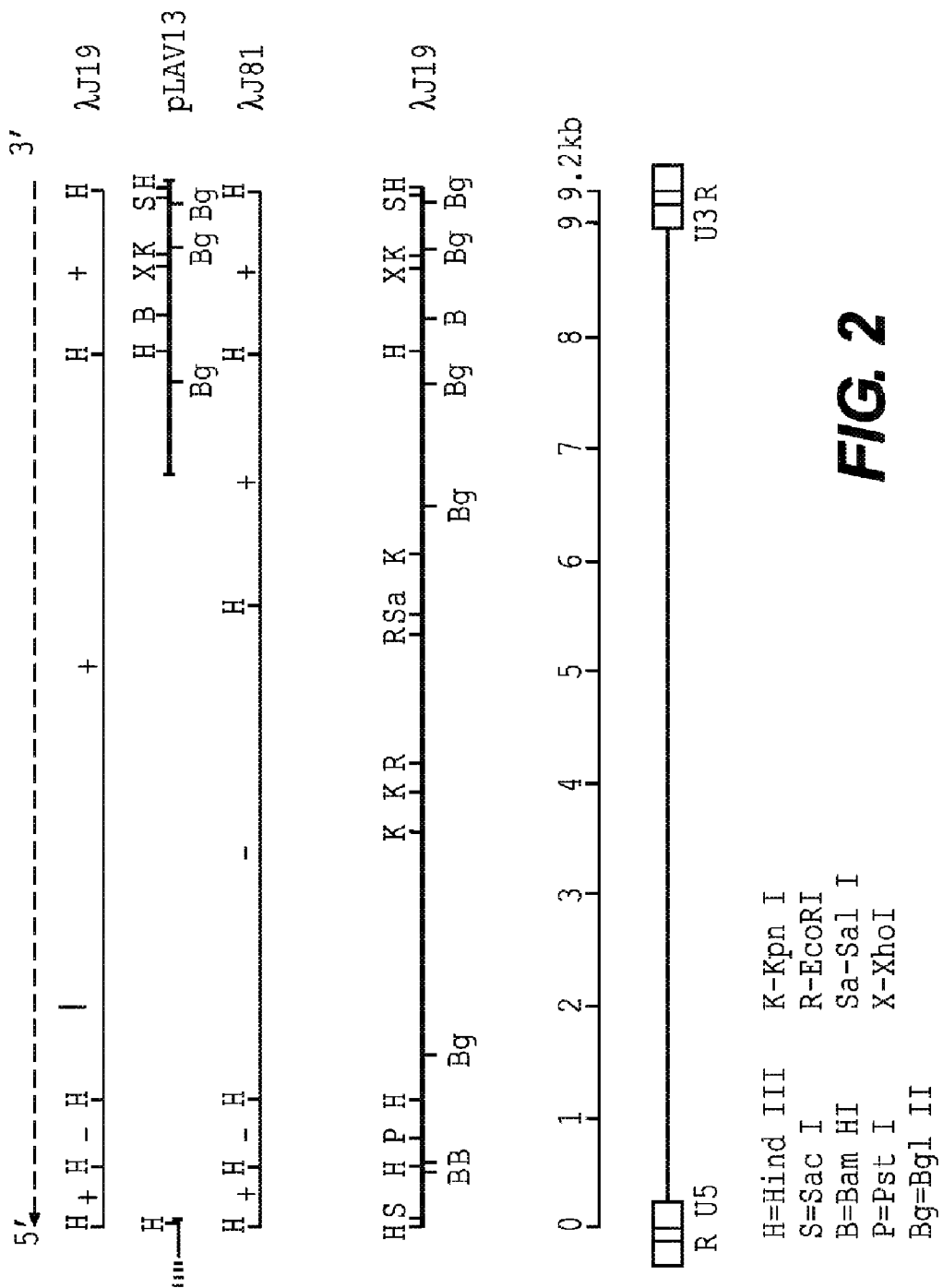

Additional features of the invention will appear in the course of the disclosure of additional features of preferred DNAs of the invention, the preparation conditions and the properties of which will be illustrated hereafter in a non-limitative manner. Reference will also be had to the drawings in which:

FIG. 1 shows restriction maps of preferred LAV inserts contained in plasmid recombinants; and FIG. 2 shows restriction maps of complete LAV fragments.

1. Construction of a cDNA Library 1.1 Virus Purification

Virions were purified from FR8, an immortalized, permanent LAV producing B-Lymphocyte line (cf. 7) (deposited at the "Collection Nationale d Cultures d Micro-organisms" of the INSTITUT PASTEUR of Paris, under Nr. I-303 on May 9, 1984). The purification protocol was described (cf. 1). The main steps were: polyethylene-glycol treatment of culture supernatant, pelleting through 20% sucrose cushion, banding on 20-60% sucrose gradient, and pelleting of the virus-containing fractions.

1.2 First-strand cDNA Synthesis

The virus associated detergent activated endogenous reaction is a technique brining into play the reverse transcriptase of the virus, after purification thereof and lysis of its envelope.

For each reaction, purified virus corresponding to 250-300 ml of FR8 supernatant was used. Final reaction volume was 1 ml. Incubation was at 37° C. for 45 min. Protein concentration was about 250 microg/ml. Buffer was: NaCl 25 mM: Tris HCl pH 7.8 50 mM, dithiothroitol 10 mM, $MgCl_2$ 6 mM, each of dATP, dGTP., dTTP at 0.1 mM, Triton X-100 0.02%: oligo dT primer 50 microg/ml. The cDNA was labelled 15 min. with alpha $^{32}$P-dCTP 400 Ci/mmole to 0.5 microM plus cold dCTP to 4 microM. Afterwards, cold dCTP was added to 25 microM to ensure optimal elongation of the first strand.

The reaction was stopped 30 min. after the dCTP chase by adding EDTA to 20 mM, SDS to 0.5%, digesting an hour with proteinase K at 100 microg/ml and phenol-chloroform extraction.

cDNA was then purified on G-50 Sephadex (Pharmacia) and ethanol precipitated.

1.3 2nd Strand Synthesis and Cloning

Purified cDNA-RNA hybrids were treated with DNA polymerase I and RNase H, according to GUBLER and HOFFMAN (cf. 17). Double-stranded DNA was dC-tailed with terminal transferase and annealed to dG-tailed Pst-digested pBR 327 (cf. 34), a derivative of pBR 322.

A cDNA library was obtained by transfection of E. coli C 600 rocBC strain.

2. Detection of LAV-specific Clones 2.1 Screening of the Library 500 recombinant clones were grown on nitrocellulose filters and in situ colony hybridization (cf. 35) was performed with another batch of cDNA made in endogenous virus-associated reaction as described (cf. 1.2) and labelled with $^{32}$P. About 10% of the clones could be detected.

A major family was obtained by small-scale amplification of these clones and cross-hybridization of their inserts. Among those clones, a major family of hybridizing recombinants was identified. Three of these cDNA clones, named pLAV 13, 75 and 82, carrying inserts of 2.5, 0.5 and 0.8 kb, respectively, were further characterized (FIG. 1).

All three inserts have a common restriction pattern at one end, indicating a common priming site. The 50 bp long common Hind III-Pst I fragment was sequenced (FIG. 1) and shown to contain a polyA stretch preceeding the cloning dC tail. The clones are thus copies of the 3' end of a polyA-RNA.

The LAV 13 specifically was shown by different assays.

The specificity of pLAV 13 was determined in a series of filter hybridization experiments using nick-translated pLAC 13 as a probe. Firstly, the probe hybridized to purified LAV genomic RNA by dot and Northern blotting (data not shown). pLAV 13 also hybridized to the genomic RNA of virus concentrated from culture supernatant directly immobilized on filters (dot blot technique). LAV RNA from different sources: normal T-cells, FR8 and other B-cell LAV producing lines, CEM cells and, although less strongly, LAV from the bone marrow culture from a haemophiliac with AIDS (cf. 3) were detected in a similar manner. Uninfected cultures proved negative. This rapid dot blot technique can be adapted with minimum difications to the detection of LAV in serum or other body fluids.

Secondly, the probe detected DNA in the Southern blots of LAV-infected T-lymphocytes and in the LAV-producing CEM cell line. No hybridization was detected in the DNA of uninfected lymphocytes nor in the DNA from normal liver (data not shown) under the same hybridization conditions.

A third characteristic resulted from the possibility of using LAV 13 to identify the whole retroviral genome of the LAV viruses as disclosed hereafter. Particularly characteristic 1.45 kb Hind III fragment which co-migrates with an internal viral fragment in Hind III cleaved pLAV 13 was detected. Bands at 2.3 and 6.7 kb were also detected. As the probe was only 2.5 kb long and as no junction fragments could be detected, it is probable that these extra-bends represent internal fragments arising from a Hind III polymorphism of the LAV genome.

Together these data show that pLAV 13 DNA is exogenous to the human genome and detects both RNA and integrated DNA forms derived from LAV infected cells. Thus, pLAV 13 is LAV specific. Being oligo-dt primed, pLAV 13 must contain the R and U3 regions of the LTR as well as the 3' end of the coding region, assuming a conventional retroviral genome structure.

Cloning of LAV Genomic DNA

Having found a HindIII site within the R region of the LTR, it was decided to clone the LAV genome by making a partial Hind III digest of proviral DNA from LAV infected cells. It was found that: (a) partial digestion increased the chance of isolating complete clones and (b) Hind III fragments were easily cloned in lambda replacement vectors. The DNA isolated from T-cells of a healthy donor after in vitro infection with LAV was partially digested with Hind III and fractionated. A 9±1.5 kb DNA containing fraction was precipitated and ligated into the Hind III arms of lambda-L47.1 (cf. 18).

The cloning of LAV genomic DNA was carried out more particularly as follows:

cDNAs were prepared from LAC infected T cells as described above, then partially digested with Hind III and fractionated on a 5-40% sucrose gradient in 10 mM Tris, Cl pH 8, 10 mM EDTA, 1 M NaCl (SW41 rotor, 16 hours at 40 000 rpm). A single fraction (9±0.5 kb) was precipitated with 20 microg/ml Dextran T40 as carrier and taken up in TE-buffer (10 mM Tris.Cl pH 8, 1 mM EDTA). Lambda-L47.1 Hind III arms were prepared by first ligating the cos sites followed by Hind III digestion and fractionation through a 5-40% sucrose gradient. Fractions containing only the lambda-Hind III arms were pooled, precipitated and taken up in TE-buffer. Ligation of arms to DNA was made at approximately 200 microg DNA/ml using a 3:1 molar excess of arms and 300 units of T4 DNA ligase (Biolabs). In vitro packaging lysates were made according to (38). After in vitro packaging the phage lysate was placed out on NM538 on a C600 rocBC strain. Approximately two million plaques were screened by in situ hybridization (cf. 39) using nitrocellulose filters. Hybridization was performed at 60° C. in 1×Denhardt solution, 0.5% SDS, 2×SSC, 2 mM EDTA. Probe: $^{32}$P nick-translated LAV insert of pLAV 13 at >$10^8$ cpm/microg: Filters were washed 2+30 minutes in 0-1 SSC, 0.1% SDS at 60° C., and exposed to Kodak XAR-5 film for 29-40 hours. Seven positive clones were identified and plaque purified on a C 600 roc BC strain. Liquid cultures were grown and the recombinant phages banded in CsCl. Phage DNA was extracted and digested under the appropriate conditions.

Seven independent clones were so derived from approximatively two million phage plaques after screening in situ with a nick-translated pLAV 13 insert as a probe. Restriction maps of lambda-J19 as well as of a Hind III polymorph lambda-J81 are shown in FIG. 2. Other recombinants lambda-J27, lambda-J31 and lambda-J57 had the same Hind III map as lambda-J19. The map of lambda-J81 is identical but for an additional Hind III site at coordinate of approximately 5 550.

The restriction maps of FIG. 2 were oriented by hybridizing blots with respect to pLAV 13 DNA.

The restriction map of the LAV 13 cDNA clone is also shown in FIG. 2. The restriction sites of lambda-J19 are: D-Bam HI, Bg-Bgl II, H-Hind III, K-Kpn I, P-Pst I, R-Eco RI, S-Sac I, Sa-Sal-I and X-Xho I. Underneath the scale is a schema for the general structure of the retroviruses showing the LTR elements U3, R and U5. Only the R/US boundary has been defined and other boundaries are only drawn figuratively.

There may be other Bam HI sites in the 5' 0.52 kb Hind III fragment of lambda-J19. They generate fragments that are too small to be detected.

FIG. 2 also shows those Hind III fragments of lambda-J19 and lambda-J81 which are detected by pLAV 13 (marked (+)), those which are not detected (−).

More particularly, lambda-J19 shows four Hind III band of 6.7, 1.45, 0.6 and 0.52 kb the first two of which correspond to bands in the genomic blot of Hind III restricted DNA. The smallest bands of 0.6 and 0.52 kb were not seen in the genomic blot, but the fact that they appear in all the independently derived clones analyzed indicates that they represent internal and not junction fragments, assuming a random integration of LAV proviral DNA. Indeed, the 0.5 kb band hybridizes with pLAV 13 DNA (FIG. 2), through the small Hind III-Pst I fragment of pLAV 13. Thus, the 0.5 kb Hind III fragment of lambda-J19 contains the R-U5 junction within the LTR.

It appears that lambda-J81 is a restriction sit polymorph of lambda-J19. Lambda-J81 shows five Hind III bands of 4.3, 2.3, 1.45, 0.6 and 0.52 kb. The 2.3 kb band is readily detected in the genomic blot by a pLAV 13 probe, but not the 4.3 kb fragment. That lambda-J81 is a Hind III polymorph and not a recombinant virus is shown by the fact that nick-translated lambda-J19 DNA hybridizes to all five Hind III bands of lambda-J81 under stringent hybridization and washing conditions. Also other restrictions sites in lambda-J81 are identical to those of lambda-J19.

Relationship to Other Human Retroviruses

HTLV-I and HTLV-II constitute a pair of C-type transforming retroviruses with a tropism for the T-cell subset, OKT4 (cf. 20). An isolate of HTLV-I has been totally sequenced (cf. 21) and partial sequencing of an HTLV-Ii has been reported (cf. 22-24). Both genomes (on LTR) were approximately 0.3 kb in length, have a pX region and show extensive sequence homology. They hybridize between themselves under reasonably stringent conditions (40% formamide, 5×SSC) and even at 60% formamide the pX regions hybridize (cf. 26). Thus, a conserved pX region is a hallmark of this class of virus.

We have compared cloned LAV DNA and cloned HTLV-II DNA (pHO (cf. 27)) by blot-hybridization and found no cross-hybridization under low stringency conditions of hybridization and washing. For example, Hind III digested lambda-J19, lambda-J27 and lambda-J81 were electrophoresed, blotted and hybridized overnight with $^{32}$P nick-translated pHO (HTLV-II) DNA (having a specific activity greater than 0.5×$10^8$ cpm/microg) in 20% formamide, 5×SSC, 1×Denhardts solution, 10% Dextran sulphate at 37° C. The washings were repeated at 50° C. and 65° C. (21). Filters were washed at 37° C. Filters were washed at 37° C. ($t_m$·50) $t_m$·50 using a 53.1% GC content derived from the HTLV-I sequence (21). The washings were repeated at 50° C. and 65° C. in 1×SSX, 0.1% SDS. Even when hybridized in 20% formamide, 8×SSC ($t_m$·50) and washed at 37° C. in 2×SSC ($t_m$·50) no hybridization was detected after two days exposure at −70° C. using an intensifying screen.

Thus, there is no molecular evidence of a relationship between LAV and the HTLV viruses. In addition, the LAV genome is approximately 9 kb long in contrast to 8.3 kb for the HTLV viruses. Despite their comparable genome sizes, LAV and Viana (cf. 29) cloned viral genomes do not cross-hybridize, nor does LAV with a number of human endogenous viral genomes (cf. 30) under non-stringent conditions (hybridization—20% formamide, 8 SSC, 37° C.: washing—2 SSC, 0.1% SDS, 37° C.

The invention also relates more specifically to cloned probes which can be made starting from any DNA fragment according to the invention, thus to recombinant DNAs containing such fragments, particularly any plasmids amplifiable in procaryotic or eucaryotic cells and carrying said fragments. As mentioned earlier, a preferred DNA fragment is LAV 13.

Using the cloned provirus DNA as a molecular hybridization probe—either by marking with radionucleotides or with fluorescent reagents—LAV virion RNA may be detected directly in the blood, body fluids and blood products (e.g. of the anti-hemophylic factors, such as Factor VIII concentrates) and vaccines, i.e. hepatitis B vaccine. It has already been shown that whole virus can be detected in culture supernatants of LAV producing cells. A suitable method for achieving that detection comprises immobilizing virus onto said a support, e.g. nitrocellulose filters, etc., disrupting the virion, and hybridizing with labelled (radiolabelled or "cold" fluorescent- or enzyme-labelled) probes. Such an approach has already been developed for Hepatitis B virus in peripheral blood (according to SCOTTO J. et al. Hepatology (1983), 3, 379-384).

Probes according to the invention can also be used for rapid screening of genomic DNA derived from the tissue of patients with LAV related symptoms to see if the proviral DNA or RNA is present in host tissue and other tissues.

A method which can be used for such screening comprises the following steps: extraction of DNA from tissue, restriction enzyme cleavage of said DNA, electrophoresis of the fragments and Southern blotting of genomic DNA from tissues, and subsequent hybridization with labelled cloned LAV proviral DNA. Hybridization in situ can also be used.

Lymphatic fluids and tissues and other non-lymphatic tissues of humans, primates and other mammalian species can also be screened to see if other evolutionary related retrovirus exist. The methods referred to hereabove can be used, although hybridization and washings would be done under non-stringent conditions.

The DNA according to the invention can be used also fro achieving the expression of LAV viral antigens for diagnostic purposes as well as for the production of a vaccine against LAV. Of particular advantage in that respect are the DNA fragments coding core (gag region) and for envelope proteins, particularly the DNA fragment extending from Kpn I (6 100) to BglII (9 150).

The methods which can be used are multifold:
a) DNA can be transfected into mammalian cells with appropriate selection markers by a variety of technique, calcium phosphate precipitation, polyethylene glycol, protoplast-fusion, etc.
b) DNA fragments corresponding to genes can be cloned into expression vectors for *E. coli*, yeast or mammalian cells and the resultant proteins purified.
c) The proviral DNA can be "shot-gunned" (fragmented) into procaryotic expression vectors to generate fusion polypeptides. Recombinant producing antigenically competent fusion proteins can be identified by simply screening the recombinants with antibodies against LAV antigens.
d) The invention also relates to oligopeptides deduced from the DNA sequence of LAV antigen-genes to produce immunogens and antigens and which can be syntethised chemically.

All of the above (a-d) can be used in diagnostics as sources of immunogens or antigens free of viral particles, produced using non-permissive systems, and thus of little or no biohazard risk.

The invention further relates to the hosts (procaryotic or eucaryotic cells) which are transformed by the above-mentioned recombinants and which are capable of expressing said DNA fragments.

Finally, it also relates to vaccine compositions whose active principle is to be constituted by any of the expressed antigens, i.e. whole antigens, fusion polypeptides, or oligopeptides.

The invention finally refers to the purified genomic mRNA, which can either be extracted as such from the LAV viruses or resynthesized back from the cDNA, particularly to a purified mRNA having a size approximating 9.1 to 9.2 kb, hybridizable to any of the DNA fragments defined hereabove or to parts of said purified mRNA. The invention also relates to parts of said RNA. The nucleotide structures of this purified RNA or of the parts thereof can indeed by deduced from the nucleotide sequences of the related cDNAs.

It will finally be mentioned that lambda-J19 and lambda-J81 have been deposited at the Collection National des Cultures de Micro-organismes (C.N.C.H.) of the Institut Pasteur, 28 Rue du Docteur Roux, 75724 Paris Cedex 15, France, under Nr. I-338 and I-339 respectively, on Sep. 11, 1984.

The invention finally refers to the genomic DNA, the DNA sequence of which can be determined and used to predict the amino acid sequences of the viral protein (antigens) and to the RNA probes which can be derived from the cDNA.

There follows the bibliography to which references have been made throughout this specification by bracketed numbers.

All the publications referred to in this bibliography are incorporated herein by reference.

REFERENCES

1. Berré-Sinoussl, F. et al. Science 220, S6S-871 (1983).
2. Mentagnler, L. et al. in Human T-cell Leukomia Viruses (eds. R. C. Gallo, M. Essex and L. Gross) p. 363-379 (Cold Spring Harbor, N.Y., 1984).
3. Vilmer, E. et al. Lancet, II, 753-757 (1984).
4. Ellrodt, A. et al. Lancet, I, 1383-1385 (1984).
5. Feorino, M. P. et al. Science, 225, 69-72 (1984).
6. Klatzmann, D. et al. Science, 225, 59-63 (1984).
7. Montagnler, L. et al. Science, 885, 63-66 (1984).
8. Brun-Vézinet, F. et al. Lancet, I, 1253-1256 (1984).
9. Kalyanaramen, V. S. et al. Science, 225, 321-323 (1984).
10. Brun-Vézinet, F. et al. Science in Press.
11. Montagnier, L., Barré-Sinoussl, F. and Chermann, J. C. in Prog. Immunodef. Res. Therapy, I, (eds. C. Griscelli and J. Vessen) p. 367-372 (Excerpta Medica, Amsterdam, 1984).
12. Popovic, M., Sarngadharan, M. G., Reed, E. and Gallo, R. C. Science, 224, 497-500 (1984).
13. Gallo, et al. Science, 224, 500-503 (1984).
14. Schüpbach, J. et al. Science, 224, 503-505 (1984).
15. Sarngadharan, M. G., Popovic, M., Bruch, L., Schüpback, J. and Gallo, R. C. Science, 223, 506-508 (1984).
16. Levy, J. A. et al. Science, 225, 840-842 (1984).

17. Gubler, U., and Hoffman, B. J. Gene, 25, 263-269 (1983).
18. Loenen, W. A. M. and Brammar, W. J. Gene, 10, 249-259 (1980).
19. Fujiyama, A. et al. Nuc. Acids Res., 11, 4601-4610 (1983).
20. Gallo, R. C. et al. Proc Natl. Acad. Sci. USA, 79, 5680-5683 (1982).
21. Selki, M., Hattorl, S., Hirayama, Y. and Yoshida, M. Proc. Natl. Acad. Sci. USA, 80, 3618-3622 (1983).
22. Haseltine, W. A. et al. Science, 225, 419-421 (1984).
23. Sodroski, J. et al. Science, 225, 421-424 (1984).
24. Shimotohno, K. et al. Proc. Natl. Acad. Sci. USA, in press.
25. Chen, I. S. Y, Mc Laughlin, J., Gasson, J. C., Clark, S. C. and Golde, D. W. Nature, 305, 502-505 (1983).
26. Shaw, G. M. et al. Proc. Natl. Acad. Sci. USA, 81, 4544-4548 (1984).
27. Gelmann, E. P., Franchini, G., Manzari, V., Wong-Stall, F. and Gallo, R. C. Proc. Natl. Acad. Sci. USA, 81, 993-997 (1984).
28. Arya, S. K. et al. Science, 225, 927-930 (1984).
29. Harris, J. D. et al. Virology, 113, 573-583 (1981).
30. Steele, P. E., Rabson, A. B., Bryan, T. and Martin, M. A. Science, 225, 943-947 (1984).
31. Montagnler, L. et al. Ann. Virol. (Institut Pasteur), 135 B, 119-134 (1984).
32. Lenz, J. et al. Nature, 302, 467-470 (1984).
33. Chen, I. S. Y., Mc Laughlin, J. and Golde, D. W. Nature, 389, 276-279 (1984).
34. Soberon, X., Covarrubias, L. and Bolivar, F. Gene, 9, 287-305 (1980).
35. Grunstein, M. and Hognhess, D. Proc. Natl. Acad. Sci. USA, 72, 3961-3965 (1975).
36. Sanger, F., Nicklen, S. and Coulsen, A. R. Proc. Natl. Acad. Sci. USA, 79, 5463-5476 (1977).
37. Southern, E. M. J. Mol. Biol., 98, 503-517 (1975).
38. Ish-Horowicz, D. and Burke, J. F. Nucl. Acids Res., 9, 2989-2998 (1981).
39. Benton, W. D. and Davis, R. W. Science, 196, 180-182 (1977).

The invention claimed is:

1. An isolated nucleic acid, wherein said isolated nucleic acid is the KpnI (at about coordinate 3500) to Bgl II (at about coordinate 6500) fragment of λ-J19.

2. A method for characterizing a biological sample comprising:
   a) providing a biological sample; and
   b) determining whether the biological sample contains HIV-1 RNA by hybridization with a labeled HIV-1 nucleic acid,
   wherein no HIV-1 RNA is detected in the biological sample.

3. The method of claim 2, wherein the biological sample comprises CD4+ T lymphocytes.

4. The method of claim 2, wherein the biological sample is blood.

5. The method of claim 2, further comprising removing cells from the biological sample.

6. The method of claim 2, further comprising culturing the biological sample.

7. A method of characterizing a biological sample from a patient comprising:
   a) providing a biological sample from a patient; and
   b) determining whether the biological sample contains HIV-1 RNA by hybridization with a labeled HIV-1 nucleic acid,
   wherein no HIV-1 RNA is detected in the biological sample.

8. The method of claim 7, wherein the biological sample comprises CD4+ T lymphocytes.

9. The method of claim 7, wherein the biological sample is blood.

10. The method of claim 7, further comprising removing cells from the biological sample.

11. The method of claim 7, wherein the biological sample is a cell culture.

12. The method of claim 7, comprising directly assaying the HIV-1 RNA in the biological sample.

13. The method of claim 7, wherein the labeled HIV-1 nucleic acid is radioactively labeled.

14. The method of claim 7, wherein the labeled HIV-1 nucleic acid is enzymatically labeled.

15. The method of claim 7, wherein the labeled HIV-1 nucleic acid is fluorescently labeled.

16. A method for selecting a biological sample in which no HIV-1 RNA id detected comprising:
   a) providing biological samples;
   b) determining whether the biological samples contain HIV-1 RNA by hybridization with a labeled HIV-1 nucleic acid; and
   c) selecting a biological sample in which no HIV-1 RNA is detected.

17. The method of claim 16, wherein the biological samples comprise CD4+ T lymphocytes.

18. The method of claim 16, wherein the biological samples are blood.

19. The method of claim 16, further comprising removing cells from the biological samples.

20. The method of claim 16, wherein the biological samples are cell cultures.

21. The method of claim 16, comprising directly assaying the HIV-1 RNA in the biological samples.

22. A method for selecting biological samples in which no HIV-1 RNA is detected comprising:
   a) providing biological samples;
   b) determining whether the biological samples contain HIV-1 RNA by hybridization with a labeled HIV-1 nucleic acid; and
   c) selecting the biological samples in which no HIV-1 RNA is detected.

23. The method of claim 22, wherein the biological samples comprise CD4+ T lymphocytes.

24. The method of claim 22, wherein the biological samples are blood.

25. The method of claim 22, further comprising removing cells from the biological samples.

26. The method of claim 22, wherein the biological samples are cell cultures.

27. The method of claim 22, comprising directly assaying the HIV-1 RNA in the biological samples.

* * * * *

UNITED STATES PATENT AND TRADEMARK OFFICE
CERTIFICATE OF CORRECTION

PATENT NO.        : 8,329,396 B1
APPLICATION NO.   : 08/052728
DATED             : December 11, 2012
INVENTOR(S)       : Alizon et al.

Page 1 of 1

It is certified that error appears in the above-identified patent and that said Letters Patent is hereby corrected as shown below:

Col. 10:

Line 25, Claim 16, replace "id" with -- is --.

Signed and Sealed this
Twelfth Day of February, 2013

Teresa Stanek Rea
*Acting Director of the United States Patent and Trademark Office*